US010080658B2

(12) United States Patent
Glazier

(10) Patent No.: US 10,080,658 B2
(45) Date of Patent: Sep. 25, 2018

(54) DEVICES AND METHODS FOR COLLAPSING PROSTHETIC HEART VALVES

(71) Applicant: St. Jude Medical, LLC, Abbott Park, IL (US)

(72) Inventor: Valerie J. Glazier, Eden Prairie, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 222 days.

(21) Appl. No.: 14/950,427

(22) Filed: Nov. 24, 2015

(65) Prior Publication Data

US 2016/0074158 A1 Mar. 17, 2016

Related U.S. Application Data

(62) Division of application No. 13/202,392, filed as application No. PCT/US2010/000475 on Feb. 19, 2010, now Pat. No. 9,265,607.

(60) Provisional application No. 61/208,101, filed on Feb. 20, 2009.

(51) Int. Cl.
*A61F 2/82* (2013.01)
*A61F 2/24* (2006.01)
*A61F 2/95* (2013.01)

(52) U.S. Cl.
CPC ............ *A61F 2/243* (2013.01); *A61F 2/2418* (2013.01); *A61F 2/2427* (2013.01); *A61F 2/2436* (2013.01); *A61F 2002/9511* (2013.01); *A61F 2002/9522* (2013.01); *A61F 2230/005* (2013.01); *A61F 2230/008* (2013.01);
(Continued)

(58) Field of Classification Search
CPC ....................................................... A61F 2/82
See application file for complete search history.

(56) References Cited

U.S. PATENT DOCUMENTS

| 5,098,440 A | 3/1992 | Hillstead |
| 5,810,873 A | 9/1998 | Morales |
| 6,187,016 B1 | 2/2001 | Hedges et al. |

(Continued)

FOREIGN PATENT DOCUMENTS

| JP | 2006507910 A | 3/2006 |
| JP | 2010-517624 A | 5/2010 |

(Continued)

OTHER PUBLICATIONS

European Examination Report for Application 10707145.8 dated Nov. 7, 2014.

(Continued)

*Primary Examiner* — Matthew Schall
(74) *Attorney, Agent, or Firm* — Lerner, David, Littenberg, Krumholz & Mentlik, LLP

(57) ABSTRACT

A crimping tool for use with a collapsible prosthetic valve having a stent frame with a plurality of cell openings, and a valve structure assembled in the stent frame. The crimping tool includes a plurality of resilient tines defining an array around a longitudinal axis of the crimping tool. The array has a first cross-section in an expanded state and a second cross-section less than the first cross-section in a collapsed state. The plurality of tines are adapted to intersect the plurality of cell openings in an assembled position of the crimping tool on the prosthetic valve to prevent pinching of the valve structure by the stent frame as the prosthetic valve is collapsed.

7 Claims, 15 Drawing Sheets

(52) U.S. Cl.
CPC . *A61F 2230/0054* (2013.01); *Y10T 29/49908* (2015.01); *Y10T 29/53996* (2015.01)

(56) References Cited

U.S. PATENT DOCUMENTS

| | | | |
|---|---|---|---|
| 7,530,253 | B2 | 5/2009 | Spenser et al. |
| 2005/0075725 | A1 | 4/2005 | Rowe |

FOREIGN PATENT DOCUMENTS

| | | | |
|---|---|---|---|
| WO | 2004/049982 | A2 | 6/2004 |
| WO | 2005/070343 | A1 | 8/2005 |
| WO | 2008/097590 | A1 | 8/2008 |
| WO | 2008150529 | A1 | 12/2008 |

OTHER PUBLICATIONS

International Search Report and Written Opinion, PCT/US2010/000475, dated May 6, 2010.
Japanese Office Action for Application No. 2011-551064 dated Aug. 29, 2014.
Japanese Office Action for Application No. 2011-551064 dated Nov. 20, 2013.
U.S. Appl. No. 11/906,133, filed Sep. 28, 2007.

(Prior Art Method)

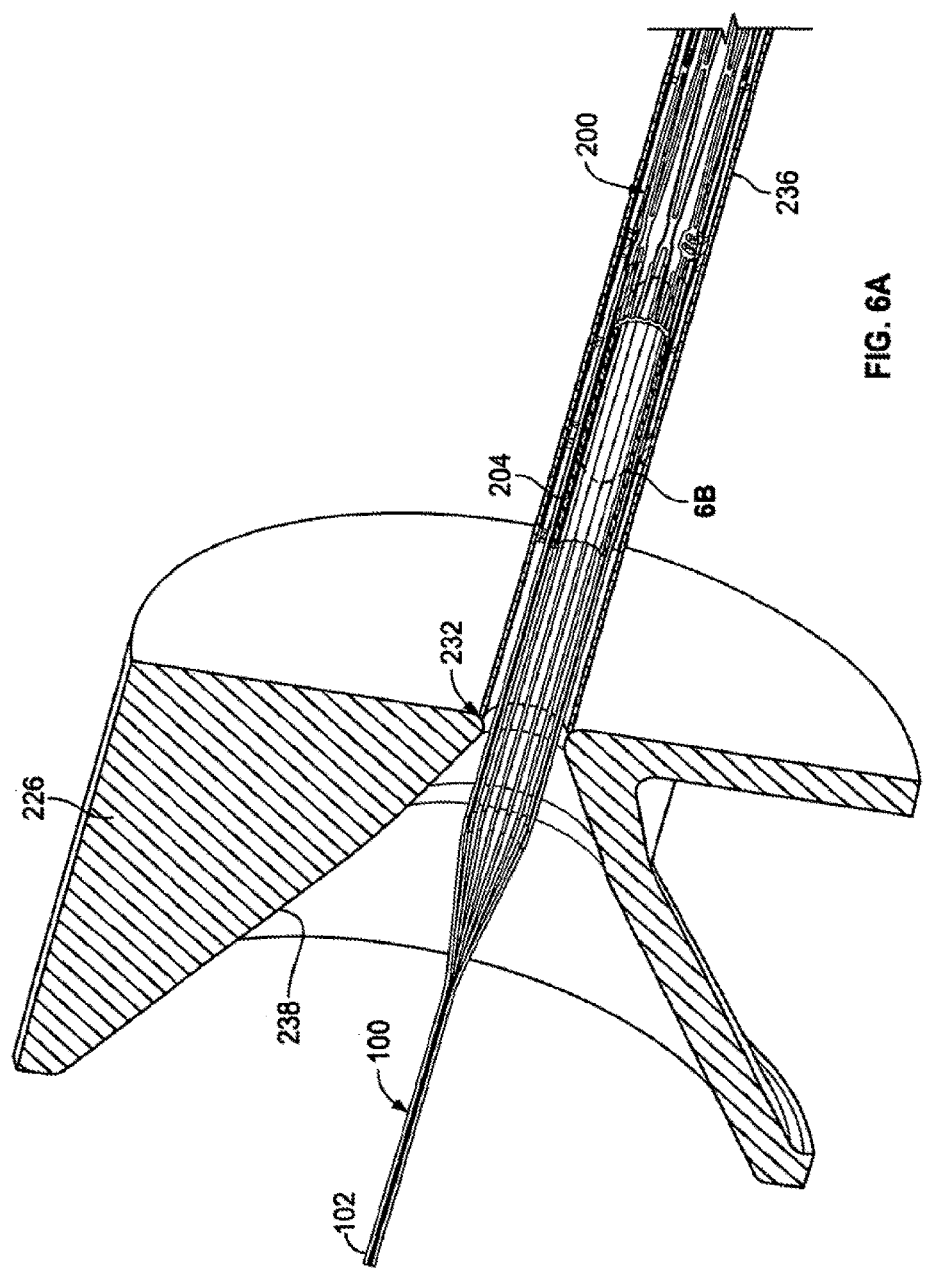

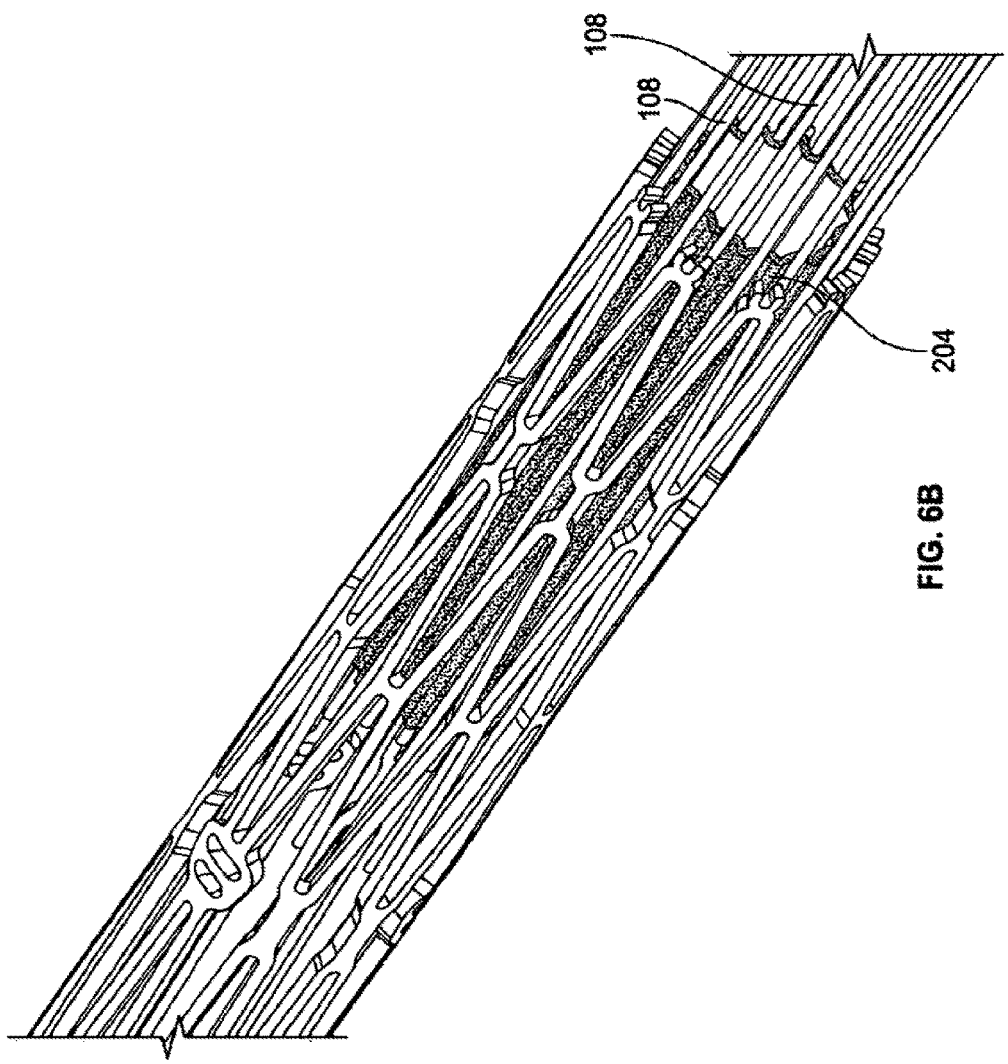

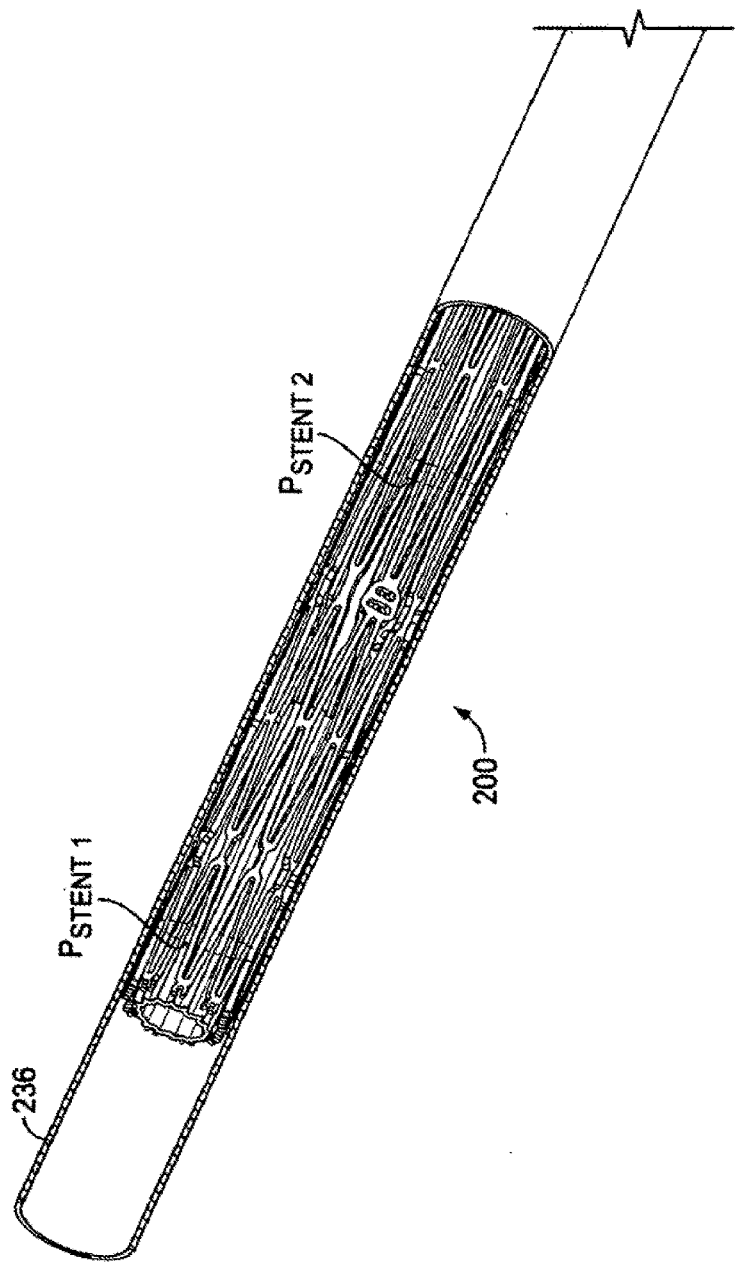

DEVICES AND METHODS FOR COLLAPSING PROSTHETIC HEART VALVES

CROSS-REFERENCE TO RELATED APPLICATIONS

This application is a divisional application of U.S. patent application Ser. No. 13/202,392, filed Aug. 19, 2011, which is a national phase application under 35 U.S.C. § 371 of International Application No. PCT/US2010/000475, filed Feb. 19, 2010, published in English, which claims the benefit of the filing date of U.S. Provisional Patent Application No. 61/208,101, filed Feb. 20, 2009, the disclosures of which are hereby incorporated herein by reference.

BACKGROUND OF THE INVENTION

The present invention is related to prosthetic heart valve replacement, and more particularly to devices, systems and methods for collapsing prosthetic heart valves.

Prosthetic heart valves that are collapsible to a relatively small circumferential size can be delivered into a patient less invasively than valves that are not collapsible. For example, a collapsible valve may be delivered into the patient via a tube-like delivery apparatus such as a catheter, a trocar, a laparoscopic instrument, or the like. This can avoid the need for a more invasive procedure such as full open-chest, open-heart surgery. When the collapsed valve has reached the desired implant site in the patient (e.g., at or near the annulus of the patient's heart valve that is to be effectively replaced by the prosthetic valve), the prosthetic valve can be released from the delivery apparatus and re-expanded to full operating size. Typically, in its full operating size, the prosthetic valve engages adjacent native tissue of the patient to firmly anchor itself in the patient.

Collapsible prosthetic heart valves typically take the form of a valve structure mounted on a stent. The stent functions as a frame to secure the valve structure. In order to deliver such a prosthetic heart valve into a tube-like delivery apparatus and ultimately the patient, the prosthetic heart valve must first be collapsed or crimped to reduce its diameter or annular perimeter. Some of the known methods and devices for accomplishing this are relatively simple. For example, it is well known in the art to use a funnel attached to a tube-like delivery apparatus to cause a gradual reduction in the diameter or annular perimeter of a stent. More complex devices, such as the one disclosed in U.S. Pat. No. 7,530,253, can also be utilized. The common goal of each of these devices and methods is to collapse the prosthetic heart valve to the smallest diameter needed (i.e., small enough to fit into the delivery tube of a delivery apparatus) without damaging the valve tissue on the stent.

Despite the various advancements and improvements that have been made to the crimping process and the overall prosthetic valve replacement process, such methods, devices, and systems suffer from similar shortcomings. Among others, valve tissue or the like is often pinched or caught within the cell openings of the stent or between the struts of the stent as the diameter or annular perimeter of the prosthetic heart valve (i.e., stent and valve tissue therein) is reduced. This phenomenon is best illustrated in FIG. 1, in which such a prosthetic heart valve 10 is illustrated in a collapsed condition. As shown, the prosthetic heart valve 10 includes valve tissue 20 attached to a stent 30. When the valve 10 is collapsed, valve tissue 20 becomes caught or pinched between the struts 31 of the stent 30 and/or within the cell openings 32 of the stent 30. The chance of damage to the tissue 20 as the prosthetic heart valve 10 is delivered to the implant site exponentially increases when this occurs. Furthermore, tissue caught within the openings can prevent the prosthetic heart valve from being reduced to the required or smallest possible diameter or annular perimeter.

Although known methods of heart valve crimping technology provide improvements over prior art systems, methods, and devices, there is a need for further improvements. Among others, the presently claimed invention addresses some of these shortcomings.

SUMMARY OF THE INVENTION

One aspect of the present invention is directed to a crimping tool for use with a collapsible prosthetic valve having a stent frame with a plurality of cell openings. The crimping tool includes a handle and a plurality of resilient tines connected to the handle. The plurality of tines define an array around a longitudinal axis, the array having a first cross-sectional size in an expanded state and a second cross-sectional size less than the first cross-sectional size in a collapsed state. The plurality of tines are adapted to intersect the plurality of cell openings in an assembled position of the crimping tool on the prosthetic valve. In preferred embodiments, the plurality of tines may define an annular array around the longitudinal axis.

Each of the plurality of tines may have a first portion that extends substantially parallel to the longitudinal axis in both the expanded and collapsed states. Each of the plurality of tines also may have a second portion disposed between the first portion and the handle, such that each of the second portions extends at an angle transverse to the longitudinal axis in the expanded state. The second portions may extend at an angle transverse to the longitudinal axis in the collapsed state.

The plurality of tines may be biased to the expanded state and move to the collapsed state upon the application of a radially inward force to the plurality of tines.

The crimping tool may further include a ring slidable relative to the plurality of tines between a first position in which the array is in the expanded state and a second position in which the array is in the collapsed state. Moving the ring from the first position to the second position exerts a radially inward force on the plurality of tines.

Optionally, the plurality of tines may include a plurality of tine pairs, a distance between the tines in each tine pair being less than a distance between adjacent tine pairs.

Another aspect of the present invention provides a system for prosthetic heart valve replacement. The system includes a collapsible prosthetic valve having a stent frame with a plurality of cell openings and a crimping tool. The crimping tool may include a handle and a plurality of resilient tines connected to the handle and defining an array around a longitudinal axis. The array has a first cross-sectional size in an expanded state and a second cross-sectional size less than the first cross-sectional size in a collapsed state. The plurality of tines are adapted to intersect the plurality of cell openings in an assembled position of the crimping tool on the prosthetic valve.

In preferred embodiments, at least some of the plurality of cell openings may have apexes and at least some of the plurality of tines are adapted to intersect the apexes of the cell openings in the assembled position. In the assembled position, each of the cell openings may be divided by a tine into a first section and a second section.

The prosthetic heart valve may further include a valve structure disposed within the stent frame. The plurality of tines may be positioned between the valve structure and the stent frame in the assembled position. Alternatively, the plurality of tines may be positioned around an exterior of the stent frame in the assembled position.

Yet another aspect of the present invention provides a method for collapsing a prosthetic heart valve having a stent frame with a plurality of cell openings, and a valve structure disposed within the stent frame. The method includes providing a crimping tool having a plurality of tines defining an array having a first cross-sectional size in an expanded state and a second cross-sectional size less than the first cross-sectional size in a collapsed state. The crimping tool is assembled to the prosthetic heart valve so that the plurality of tines intersect the cell openings to divide the cell openings into first and second sections. A radially inward force is applied to the prosthetic heart valve in order to collapse the prosthetic heart valve while the crimping tool is assembled thereto.

In embodiments of the prosthetic heart valve in which at least some of the cell openings have apexes, the crimping tool may be assembled to the prosthetic heart valve so that at least some of the plurality of tines intersect the apexes. The plurality of tines may be inserted between the valve structure and the stent frame, or may be positioned around an exterior of the stent frame.

BRIEF DESCRIPTION OF THE DRAWINGS

FIGS. 6, 6A, 6B, and 6C are schematic illustrations showing a method of inserting a prosthetic valve into a catheter in accordance with an embodiment of the present invention.

DETAILED DESCRIPTION

Figure 2:
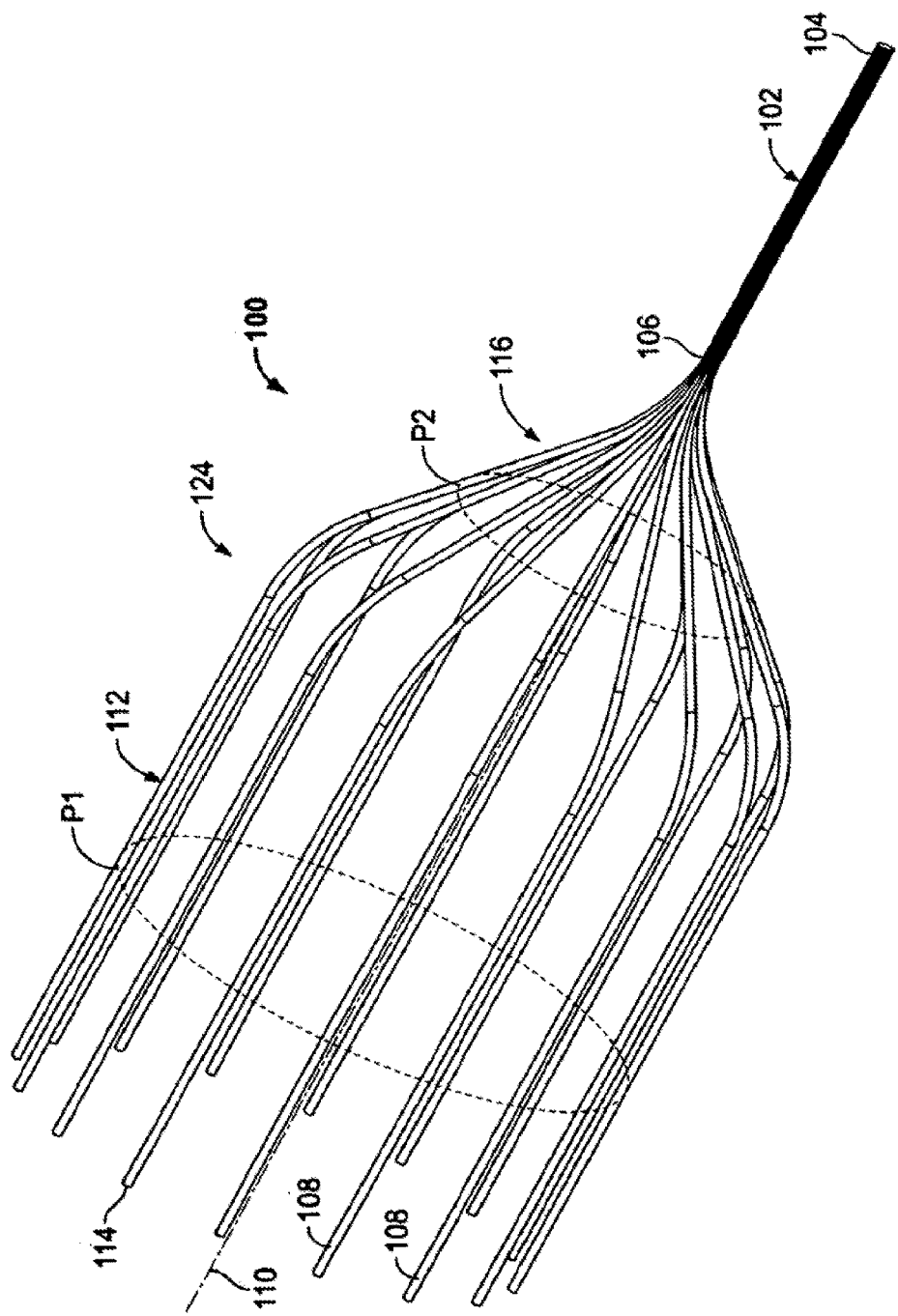
FIG. 2 is a perspective view of a crimping tool according to one embodiment of the present invention, shown in an expanded state.

Referring now to FIG. 2, there is shown a crimping tool 100 according to an illustrative embodiment of the present invention. Crimping tool 100 prevents tissue impingement during collapse of a prosthetic heart valve for delivery into a patient. Crimping tool 100 has a handle or stem 102 with a free end 104 and another end 106. A plurality of long, thin tines 108 extend in an array from end 106 of the stem. Specifically, tines 108 are arranged around the central longitudinal axis 110 along which the stem 102 extends. Tines 108 preferably define an annular array having a substantially cylindrical configuration around central axis 110, but other configurations including, but not limited to, oval and elliptical configurations are also contemplated herein.

In the embodiment shown, sixteen tines 108 are positioned around the central axis 110. However, this number is not critical, and as few as two tines or more than sixteen tines may be used. The number of tines on the crimping tool 100 may vary widely based, in part, upon the actual size of the tines and the number and size of the cell openings formed in the stent portion of the prosthetic heart valve, as discussed more fully below. In preferred embodiments, however, crimping tool 100 will have at least one tine 108 for each column of cell openings formed around the circumference of the stent.

Figure 2A:
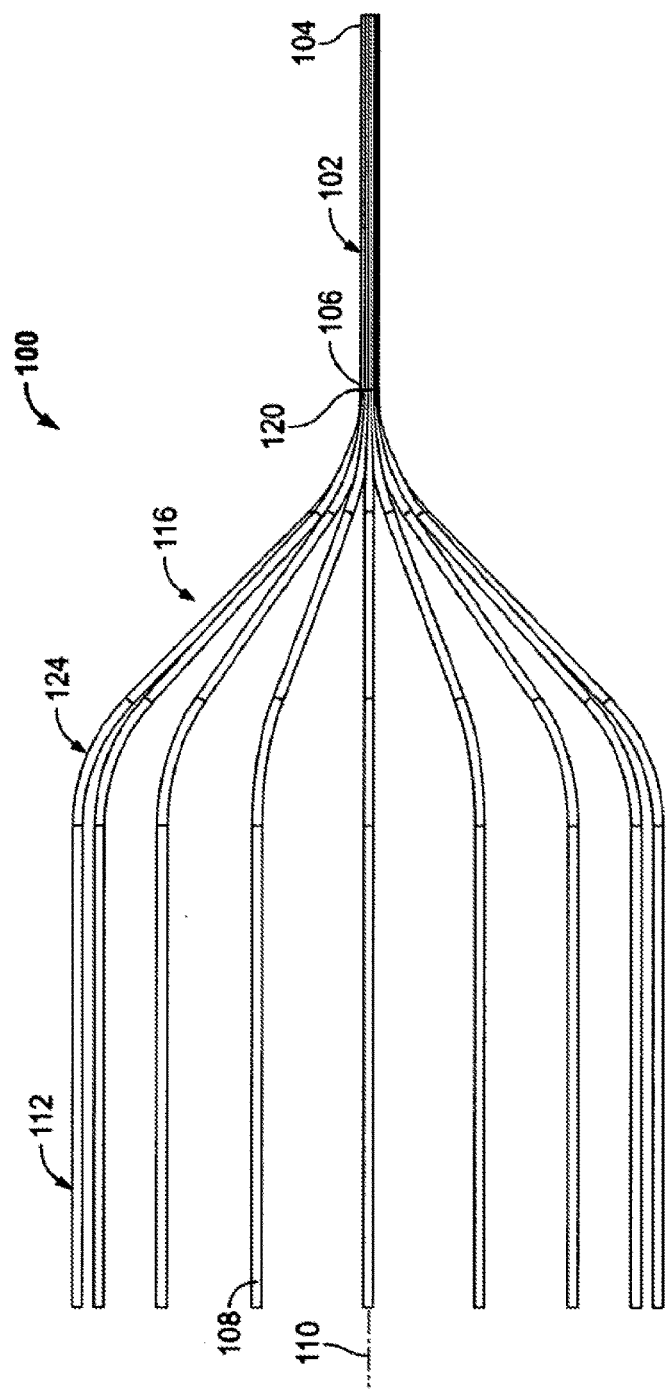
FIG. 2A is a side elevational view of the crimping tool shown in FIG. 2.

Referring to FIG. 2A, each of the tines 108 has a first portion 112 with a tip 114 and a second portion 116. First portions 112 may extend substantially parallel to one another and to the central axis 110. Second portions 116, on the other hand, are transverse to central axis 110 and converge together at a converging point 120 at which they join to stem 102. A transition region 124 demarcates the transition between the first portion 112 and the second portion 116 of each tine 108. It is to be appreciated that although the lengths of tines 108 in the preferred embodiment are uniform, the tines 108 may differ in length, such that one or more of the tines 108 may be shorter or longer than the others.

The angle between second portions 116 and central axis 110 is not critical. However, the combination of that angle and the length of second portions 116 must be sufficient that, with tines 108 in the expanded state described below, the cross-section defined by the first portions 112 of the tines is large enough to assemble the tines to a prosthetic heart valve in the manner described below.

As shown in FIGS. 2 and 2A, in a preferred embodiment, the tines 108 form an annular array around the central axis 110, such that crimping tool 100 has an overall circular cross-section. The circular cross-section will differ at different locations along the length of crimping tool 100. For example, crimping tool 100 defines an annular perimeter P1 around the first portions 112 of the tines 108 which, in the expanded state, is preferably greater than the annular perimeter P2 defined at any point around the second portions 116. Preferably, annular perimeter P1 is substantially uniform along the length of the first portions 112. Annular perimeter P2, on the other hand, will incrementally decrease along transition region 124 from first portions 112 to converging point 120.

Each individual tine 108 may have a circular cross-section along its entire length. It is to be appreciated, however, that each of the tines 108 may possess a different shaped cross-section and/or may vary in shape and/or thickness throughout the length of the tine. For example, each of the tines 108 may have an oval, triangular, rectangular, or any other cross-section. Further, the thickness of one or more tines 108 in their first portions 112 may be greater than or less than the thickness of the same tines 108 in their second portions 116. In addition, the shape and/or thickness of one or more tines 108 may be different from the shape and/or thickness of other tines.

The tips 114 of tines 108 are preferably rounded to prevent damage to tissue they may contact when inserted into a prosthetic heart valve. Alternatively, the tips 114 may take on any other profile, such as a tapered profile, so as to better enable the tines 108 to extend into the prosthetic heart valve, as described in more detail herein.

Figure 3:
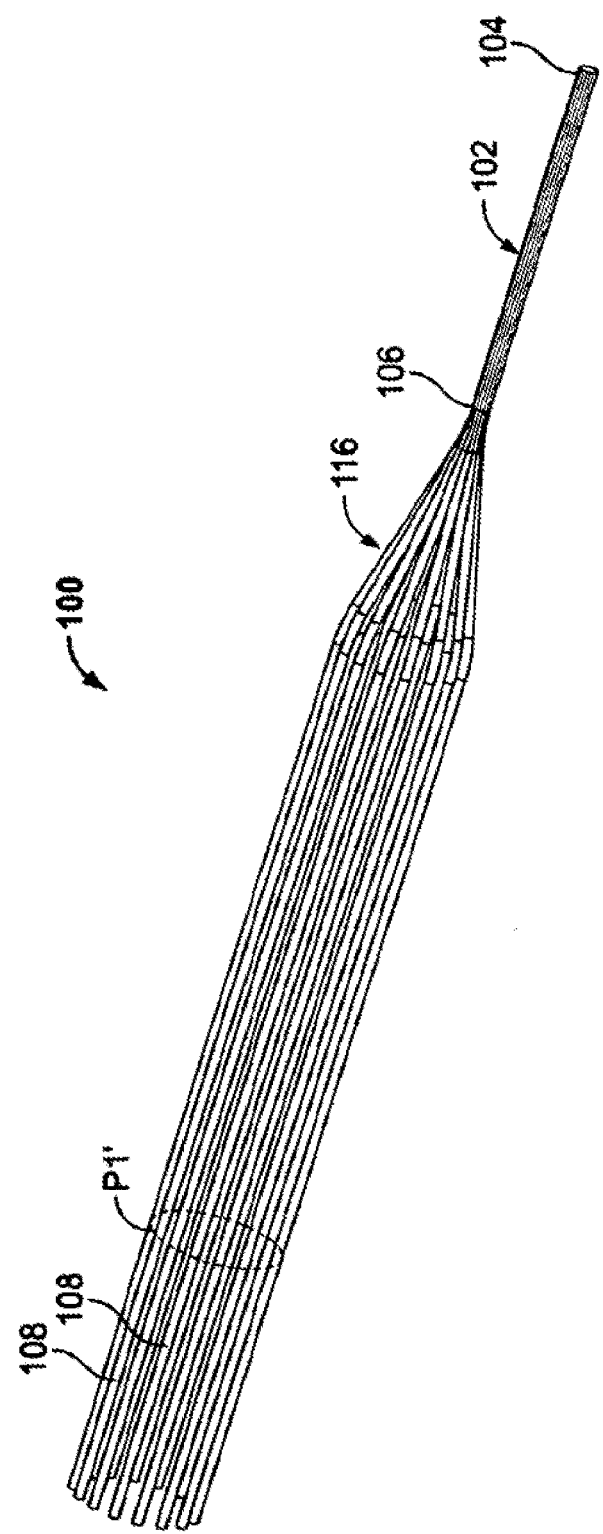
FIG. 3 is a perspective view of the crimping tool of FIG. 2, shown in a compressed state.

Each of tines 108 is preferably resilient and biased to the expanded state, such that the tines 108 may move radially inwardly toward the central axis 110 of crimping tool 100 upon the application of an external force, as illustrated in the collapsed or compressed state of the crimping tool 100 shown in FIG. 3, and then return to their uncompressed or expanded state shown in FIG. 2 once the crimping tool has served its purpose and the external force has been removed. It will be appreciated that tines 108 need not necessarily be formed of a resilient material. Rather, tines 108 may be formed from a relatively rigid material in first portions 112, and from a resilient material in transition regions 124 and second portions 116. These resilient portions preferably would be biased to the expanded or uncompressed state shown in FIG. 2. In such arrangement, the second portions 116 will be able to deform upon application of an external force so as to bring the first portions 112 closer to central axis 110. In a preferred embodiment, however, tines 108 are formed from the same material along their entire length, the material having sufficient resiliency to cause first portions 112 to move toward central axis 110 upon the application of an external force. As will be discussed in more detail below, any external force can be used to cause inward radial movement of the tines 108 toward the collapsed state.

The annular perimeter P1 of crimping tool 100 in the uncompressed or expanded state will be greater than its annular perimeter P1' in the compressed or collapsed state. As will be discussed in more detail below, the ability of crimping tool 100 to collapse to a smaller perimeter P1' is necessary for the crimping tool 100 to be compressed along with a prosthetic heart valve by an amount sufficient to fit into a delivery catheter or the like.

As noted above, in preferred embodiments, crimping tool 100 may be formed from resilient materials or from materials exhibiting elastic properties so as to enable tines 108 to reversibly deform. One such material in this regard is nitinol. Other metals such as stainless steel or the like also may be used, as may tough and resilient polymers, such as polyurethanes, polyethylenes, nylons or any combination of resins, core or fiber reinforced materials. Furthermore, the crimping tool 100 may be entirely or partially coated with a material or materials selected to provide desirable characteristics. In one embodiment, as will be explained in greater detail below, to avoid damage to the valve tissue when the crimping tool 100 is inserted into a prosthetic valve, all or portions of the crimping tool 100 may be coated with a material which can minimize friction. Such coating may include, without limitation, fluorinated ethylene propylene (FEP) or polytetrafluoroethylene (PTFE).

Figure 4:
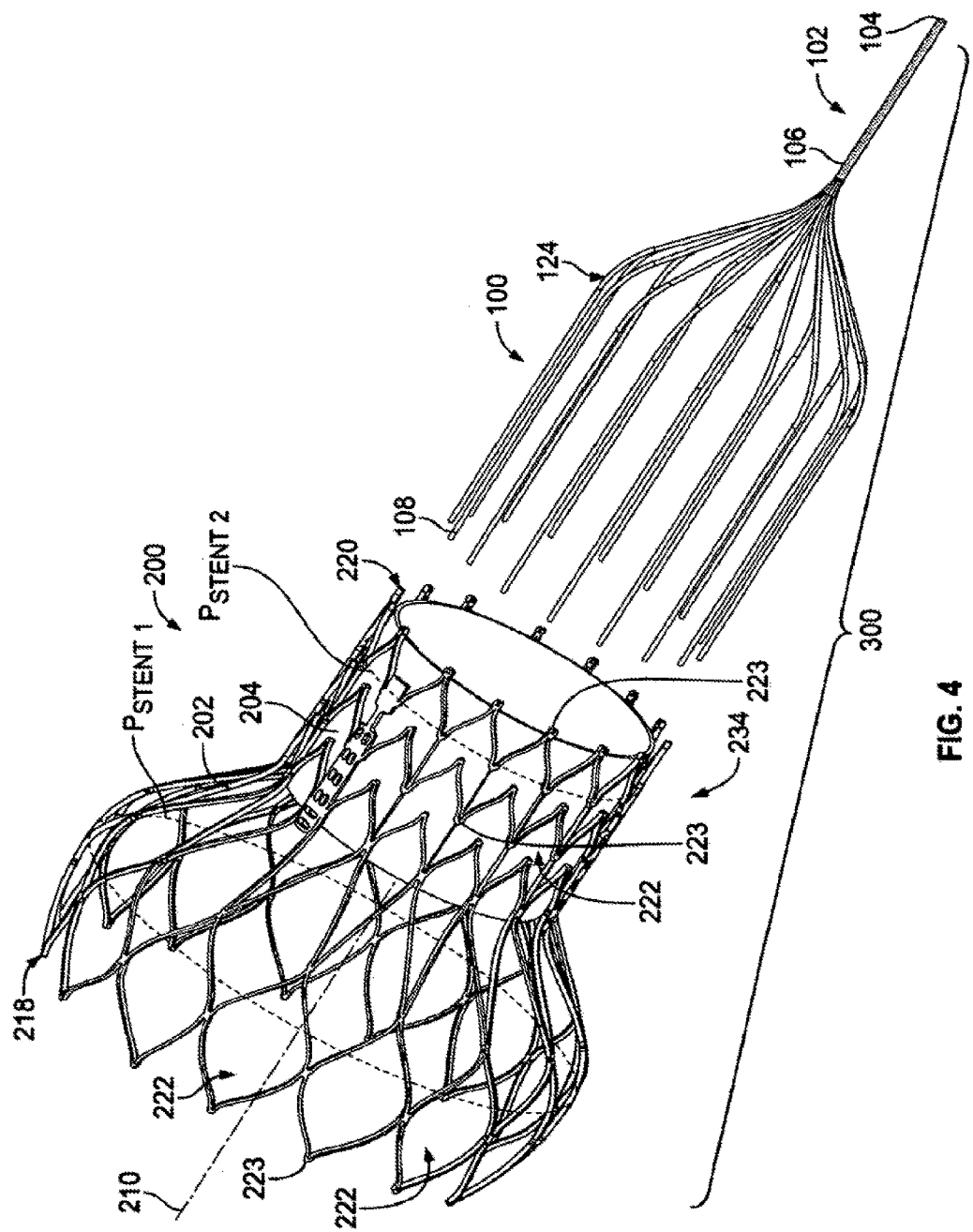
FIG. 4 is a perspective exploded view of a system, including a collapsible valve and a crimping tool, according to an embodiment of the present invention.

Referring now to FIG. 4, a system 300 for valve replacement is shown in accordance with the present invention. System 300 includes a collapsible (and re-expandable) prosthetic heart valve 200 and a crimping tool, such as crimping tool 100 described above.

The collapsible prosthetic heart valve 200 may be any collapsible prosthetic heart valve known in the art, such as those disclosed in commonly assigned application Ser. No. 11/906,133 filed on Sep. 28, 2007 and entitled "Collapsible-Expandable Prosthetic Heart Valves With Structures For Clamping Native Tissue" and WO 2008/150529 published on Dec. 11, 2008 and entitled "Prosthetic Heart Valves," the disclosures of which are incorporated herein by reference. Preferably, collapsible prosthetic heart valve 200 includes at least: (1) a frame or stent 202 having a distal end 218 and a proximal end 220; and (2) a valve 234 formed from softer materials. Valve 234 may include a ring or cuff 204 which terminates at or near the proximal end 220 of stent 202, and a plurality of leaflets (not shown) attached inside of the cuff and cooperating with one another to permit blood flow in one direction through valve 200, but not in the opposite direction. Cuff 204 and the valve leaflets may be formed from tissue, such as bovine or porcine pericardial tissue; fabric, such as polyester; or other suitable biocompatible materials. Any means of attachment known in the art may be used to attach cuff 204 and the valve leaflets to stent 202, such as sewing with suture material. It is to be appreciated that when a "collapsible prosthetic heart valve" is referred to herein, it is intended to include at least a stent 202 or other collapsible support structure and a valve 234 formed from softer materials and positioned within the stent 202. Where needed, specific reference may be made herein to the specific components of the collapsible prosthetic heart valve, such as the "cuff," "leaflets," or "tissue."

Stent 202 has a central axis 210 that extends in the length direction, and may have a larger diameter adjacent distal end 218 than the diameter adjacent proximal end 220. This provides stent 202 with an annular perimeter $P_{STENT1}$ at or near its distal end 218 that is greater than the annular perimeter $P_{STENT2}$ at or near its proximal end 220.

Stent 202 preferably includes collapsible cell openings 222 defined along the length and around the circumference of the stent. The cell openings 222 may all have the same shape or may differ in shape in different portions of the stent. For example, as shown in FIG. 4, stent 202 may have diamond-shaped cell openings adjacent distal end 218 and generally arrow-shaped openings adjacent proximal end 220. As shown, both the diamond-shaped and arrow-shaped cell openings 222 include apexes 223. It will be appreciated, however, that stent 202 may have any shape or size of cell openings 222, including those without apexes.

Figure 5:
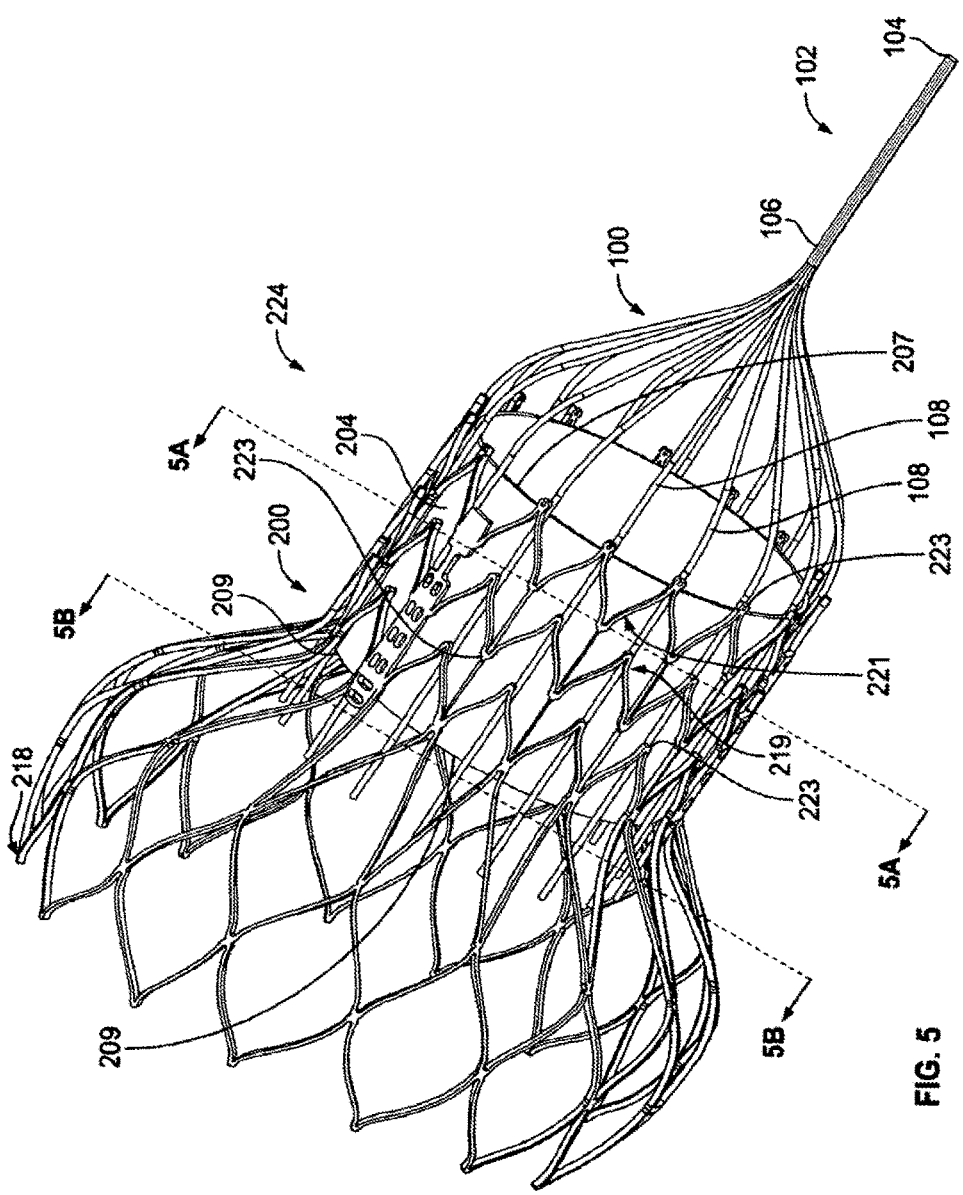
FIG. 5 is a perspective view depicting the system of FIG. 4 in the assembled condition.

Referring to FIG. 5, the crimping tool 100 is shown positioned within the prosthetic heart valve 200. To position the crimping tool 100 within the prosthetic heart valve 200, the crimping tool 100 can be manually inserted in its uncompressed or expanded state into the prosthetic heart valve 200. First, a surgeon or technician may grasp the stem 102 of the crimping tool 100 such that the first portions 112 of the tines 108 face in a direction away from the surgeon. Second, turning to both FIGS. 5 and 5A, each of the tines 108 may then be inserted between the cuff 204 and stent 202, such that the plurality of tines 108 may directly contact and/or be adjacent the outer surface of the cuff 204 and the inner surface of the stent 202.

When inserting the crimping tool 100 between the cuff 204 and stent 202, it is preferred that each of the plurality of tines 108 be positioned generally at or near the longitudinal centerline of a cell opening 222 of the stent. With reference to FIG. 5, each of the tines 108 on the crimping tool 100 may be in radial alignment with the apexes 223 of the cell openings 222 such that the areas of the cell openings 222 are divided into two distinct sections, i.e., a first section 219 and a second section 221. It will be appreciated that the tines 108 do not have to be perfectly aligned with the longitudinal centerlines of the cell openings 222 and/or the apexes of the cell openings. The tines 108 may be considered to be appropriately positioned when they cover or block a portion of the cell openings 222. As will be discussed in more detail herein, any reduction in the area of the cell openings 222 can be beneficial.

The tines 108 preferably may be advanced into the prosthetic heart valve 200 until the transition regions 124 of the tines are at or near the proximal end 220 of the stent 202. Alternatively, the crimping tool 100 may be advanced until it cannot be advanced any further into the stent 202, or up until a point where the crimping tool 100 is considered to be sufficiently positioned between the cuff 204 and stent 202. Once the final position of the crimping tool 100 within the prosthetic heart valve 200 is established, first portions 112 of the crimping tool 100 preferably extend beyond the distal edge 209 of the cuff 204 so that all or substantially all of the cell openings 222 overlying cuff 204 are divided by at least one tine 108. In the fully assembled position shown in FIG. 5, the second portions 116 of tines 108 and the stem 102 may be positioned proximally of the proximal end 220 of the stent 202.

Figure 6:
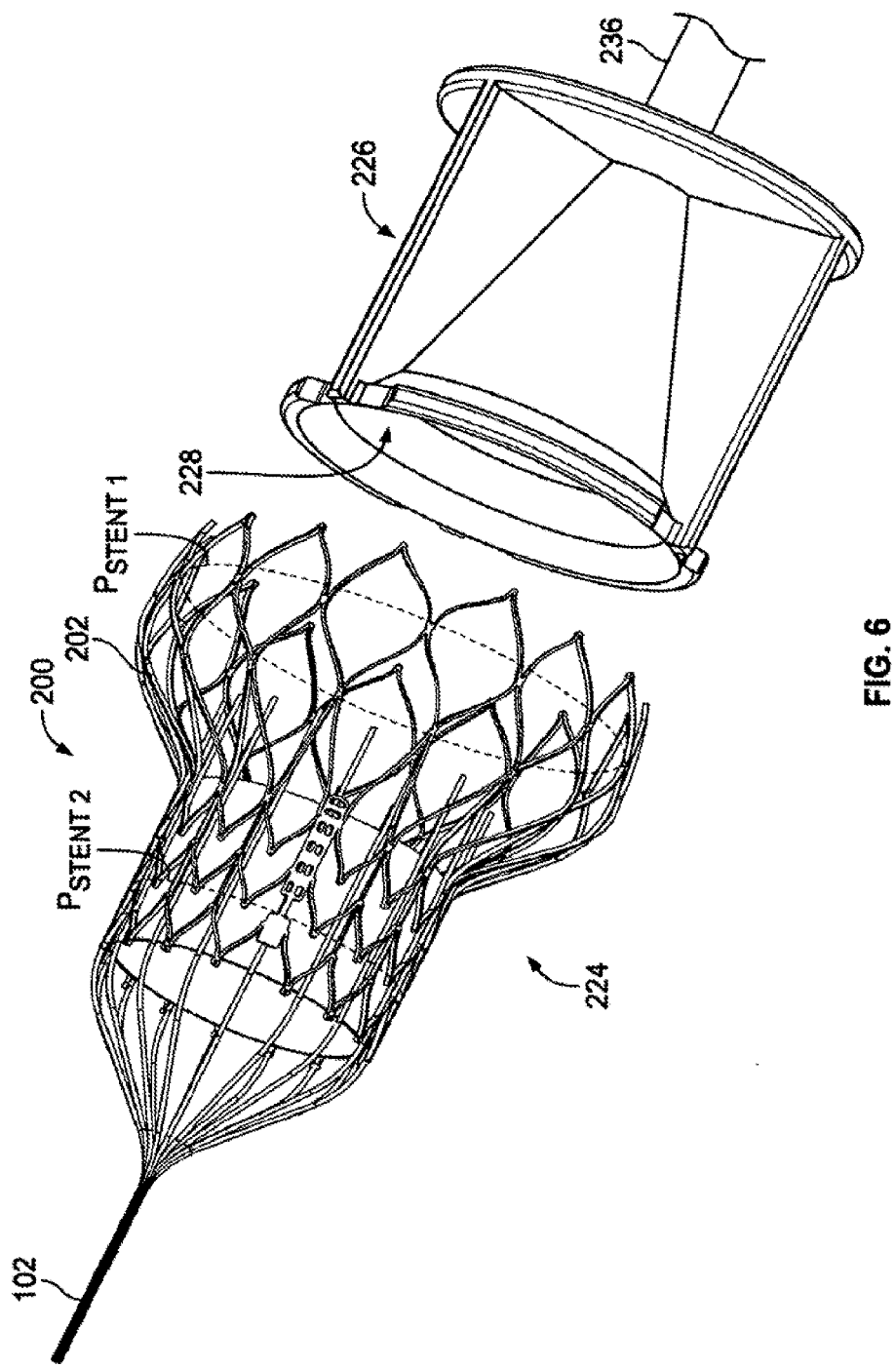

With the crimping tool 100 in the assembled position on the prosthetic heart valve 200, the prosthetic heart valve is ready to be crimped to the collapsed state, and with it crimping tool 100. FIGS. 6, 6A, and 6B schematically illustrate one embodiment of a technique for crimping the prosthetic heart valve/crimping tool combination 224 to the collapsed state and loading the prosthetic heart valve 200 into a delivery catheter 236 or the like for eventual insertion into a patient's body. In order for the crimping tool/prosthetic heart valve combination 224 to fit into the delivery catheter 236, the annular perimeters $P_{STENT1}$ and $P_{STENT2}$ of the prosthetic heart valve 200, as well as the overall circumference of the crimping tool 100, must first be reduced in size. This can be accomplished by loading the crimping tool/prosthetic heart valve combination 224 into a crimping device capable of radially collapsing the crimping tool/prosthetic heart valve combination. Referring to FIG. 6, in one embodiment, a funnel 226 having a large diameter opening 228 at one end and a small diameter opening 232 on the opposite end may be used as the crimping device. The small diameter opening 232 may be connected to the delivery catheter 236 so that as the collapsed crimping tool/prosthetic heart valve combination 224 emerges from the funnel 226, it will immediately enter the delivery catheter without any opportunity to radially expand.

To load the crimping tool/prosthetic heart valve combination 224 into the funnel 226, a surgeon may grasp the stem 102 of the crimping tool 100 and use it to maneuver the crimping tool/prosthetic heart valve combination into the large diameter opening 228 of the funnel 226. Preferably, the prosthetic heart valve 200 is oriented so that the distal end 218 thereof is the first to enter the large diameter opening 228 of funnel 226. This orientation enables the prosthetic heart valve 200 to be pushed against the second portions 116 of tines 108 as the heart valve is being collapsed, thereby keeping the heart valve from being pulled off of crimping tool 100. This orientation also permits stem 102 of crimping tool 100 to be accessible for removing the crimping tool from the heart valve once the heart valve is in place in delivery catheter 236. The accessibility of the stem 102 also may eliminate the need for a secondary tool to transport the prosthetic heart valve 200 and minimizes unnecessary contact with the tissue of the cuff 204, although a secondary tool can be used if desired.

Figure 1:
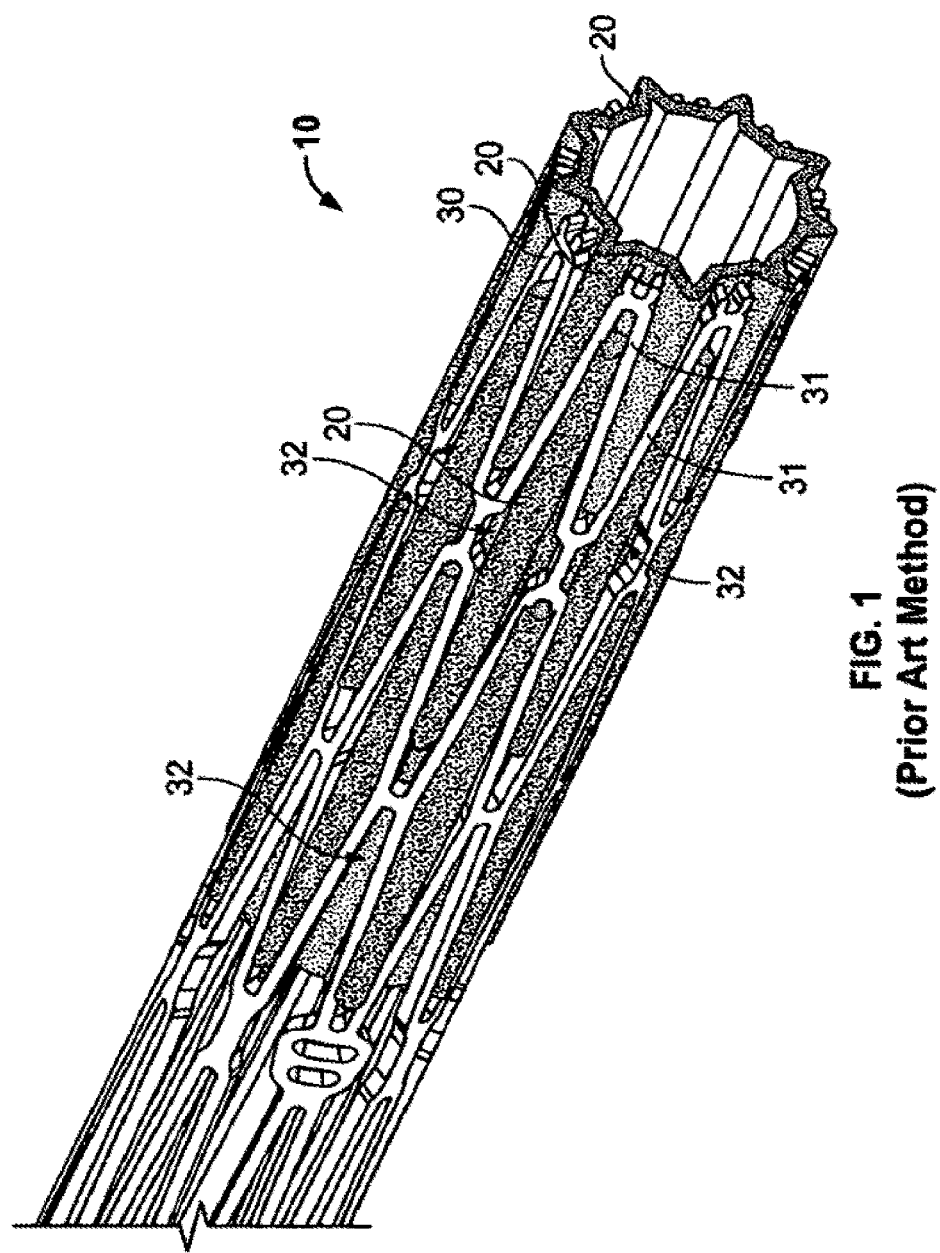
FIG. 1 is a perspective view of a portion of a prosthetic heart valve which has been crimped using a prior art technique.

Referring to FIG. 6A, as the crimping tool/prosthetic heart valve combination 224 advances through the funnel 226, the converging walls 238 of the funnel will apply a compressive force causing the stent 202 and tines 108 to begin to collapse and the overall annular perimeters $P_{STENT1}$ and $P_{STENT2}$ to be reduced. Collapsing will continue until the crimping tool/prosthetic heart valve combination 224 reaches a size sufficiently small in diameter to pass through the small diameter opening 232 of the funnel. During the collapsing process, the presence of tines 108 intersecting cell openings 222 will reduce the continuous open area of the cell openings, thereby making it more difficult for the tissue cuff 204 to enter the cell opening where it can be pinched by the struts of stent 202 as it collapses, all of which can be seen in FIG. 6B. Thus, in contrast to the prior art method of FIG. 1, the tines 108 of crimping tool 100 prevent the tissue of cuff 204 from being pinched and damaged by the stent 202 as the prosthetic heart valve 200 is collapsed.

As the crimping tool/prosthetic heart valve combination 224 passes through small diameter opening 232, it will exit funnel 226 and enter the lumen of delivery catheter 236. Advancement of the crimping tool/prosthetic heart valve combination 224 may continue until prosthetic heart valve 200 is entirely within delivery catheter 236 or until it is determined that crimping tool/prosthetic heart valve combination 224 is located within the delivery catheter 236 by a sufficient amount. When the crimping tool/prosthetic heart valve combination 224 is at an appropriate location within the delivery catheter 236, the surgeon may simply pull the crimping tool 100 proximally away from the prosthetic heart valve 200 using the stem 102. Referring to FIG. 6C, when the crimping tool 100 has been freed from the prosthetic heart valve 200, only the prosthetic heart valve will remain within the delivery catheter 236. As shown, annular perimeters $P_{STENT1}$ and $P_{STENT2}$ will be substantially equal in size, as the entirety of the prosthetic heart valve 200 must fit within the delivery catheter 236 which, as shown, has a substantially uniform cross-section.

It is to be appreciated that there are numerous crimping devices other than funnel 226 that can be utilized in accordance with the present invention. For example, without limitation, the HV500 crimper available from Machine Solutions, Inc., also known as an "iris crimper", is one such alternative crimping device.

The above-described collapsing or crimping of the prosthetic heart valve 200 and/or crimping tool 100 are preferably elastic deformations. For example, the stent 202 and crimping tool 100 are preferably resiliently biased to have about the same diameter and shape, respectively, in the expanded state. In such a case, collapsing of the prosthetic heart valve 200 and crimping tool 100 can be accomplished by elastic deformation of the stent 202 and crimping tool 100, e.g., by applying a force to the prosthetic heart valve and crimping tool directed radially inwardly, such as by confining the stent 202 and crimping tool 100 within a passageway, such as a funnel or tube, having a smaller annular perimeter or diameter than the fully expanded stent and crimping tool. When the prosthetic heart valve 200 and/or crimping tool 100 is pushed or pulled out of the confined passageway, the stent 202 and crimping tool 100 may re-expand automatically and elastically to their full size. It is to be appreciated that expansion of the stent 202 and/or crimping tool 100 may be at least partly assisted by other means.

Figure 5A:
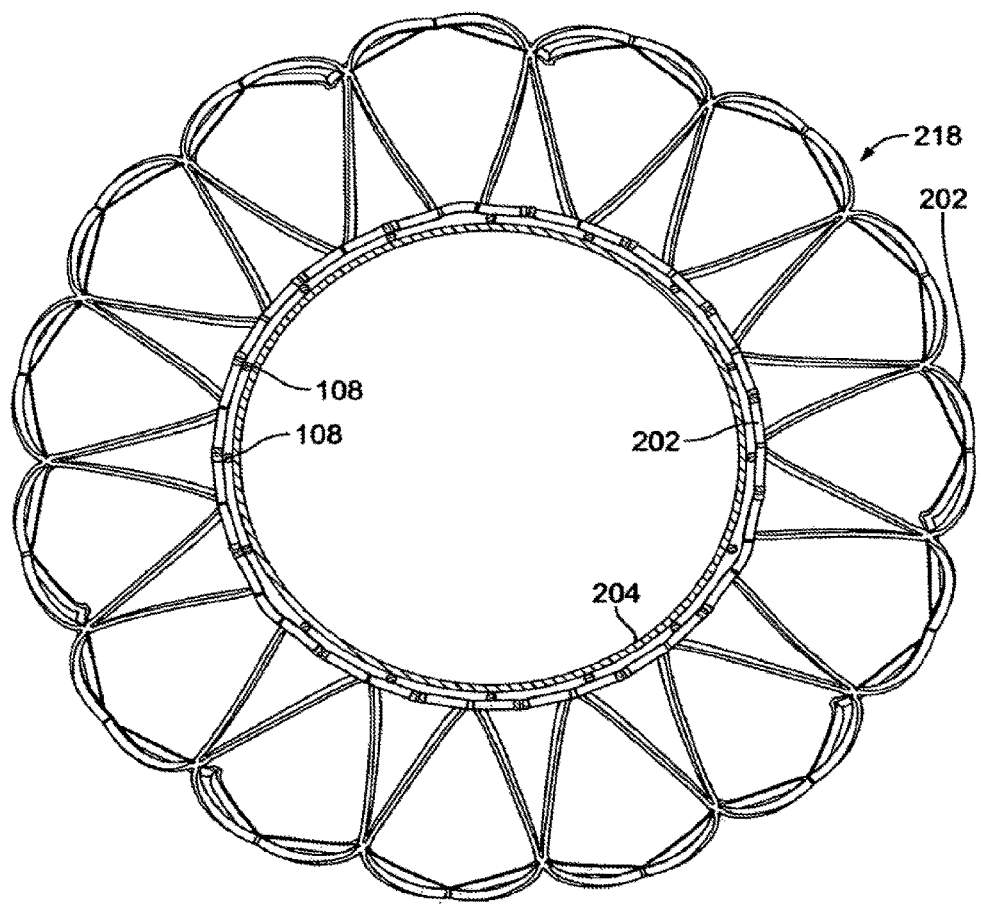
FIG. 5A is a cross-sectional view taken along line 5A-5A of FIG. 5.
Figure 5B:
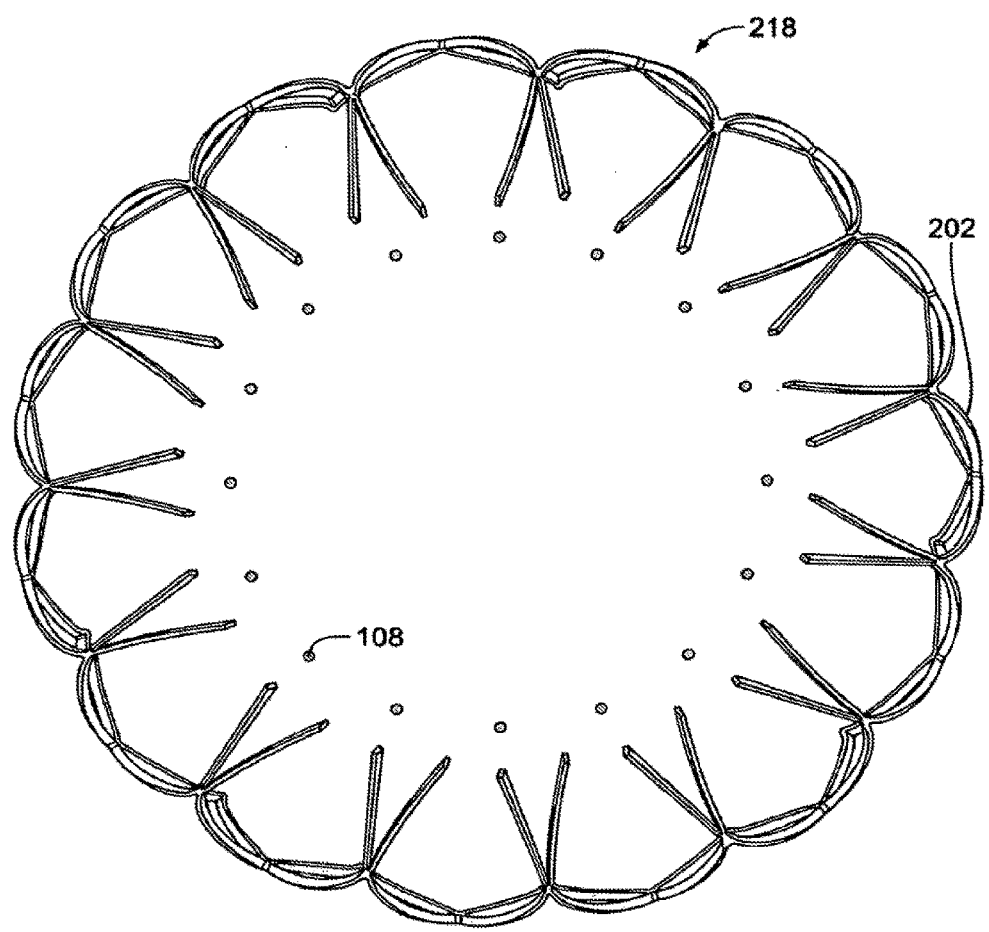
FIG. 5B is a cross-sectional view taken along line 5B-5B of FIG. 5.

During the crimping process, the overall shape of the annular perimeter or diameter of the stent 202 and crimping tool 100 may remain substantially the same in the expanded state and the collapsed state. For example, as shown in FIG. 5A, the crimping tool/prosthetic heart valve combination 224 has an overall circular cross-section in the expanded state. In the collapsed state, as shown in FIG. 6A, the cross-section may remain substantially circular. However, this need not be the case. That is, the crimping tool 100 and/or prosthetic heart valve 200 may, for example, have an elliptical cross-section in the expanded state, but may collapse to a substantially circular cross-section.

Figure 7:
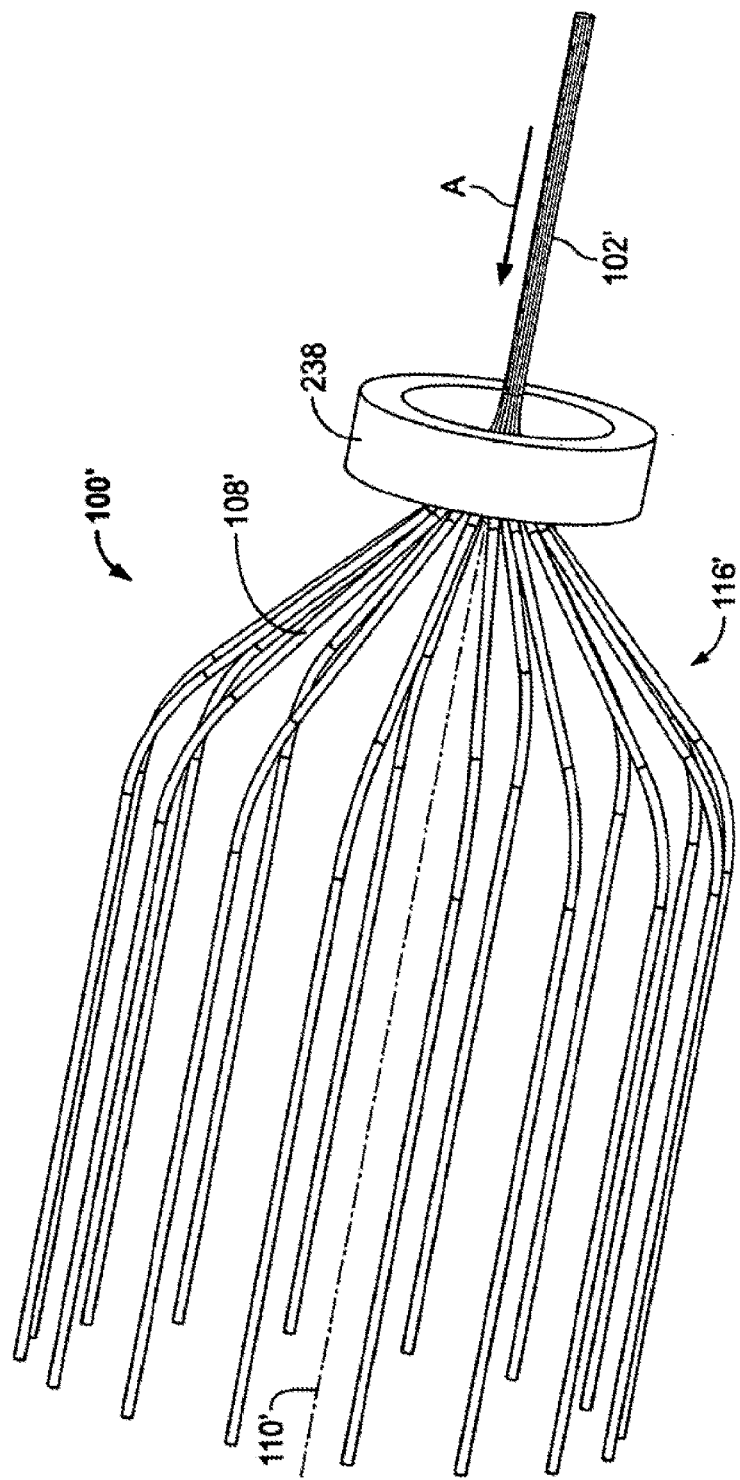
FIG. 7 is a perspective view of a crimping tool in accordance with another embodiment of the present invention.

In an alternative method of loading the prosthetic heart valve/crimping tool combination 224 into a crimping device, the prosthetic heart valve/crimping tool combination may be initially compressed using a secondary crimper. Thus, referring to FIG. 7, a crimping tool 100' may include a ring 238 disposed for advancement along the length of the stem 102' in the direction of arrow A. As the ring 238 is pushed against the second portions 116' of tines 108', the force exerted by the ring causes each of the tines to move radially inwardly toward the central axis 110' of the crimping tool 100'. In a preferred arrangement, the ring 238 will be slid along the tines 108' when the prosthetic heart valve/crimping tool combination is first inserted into a crimping device, such as funnel 226. In such event, the force exerted by the converging walls of the funnel, as well as the force applied by the ring 238, will act together to collapse the prosthetic heart valve/crimping tool combination.

Figure 8:
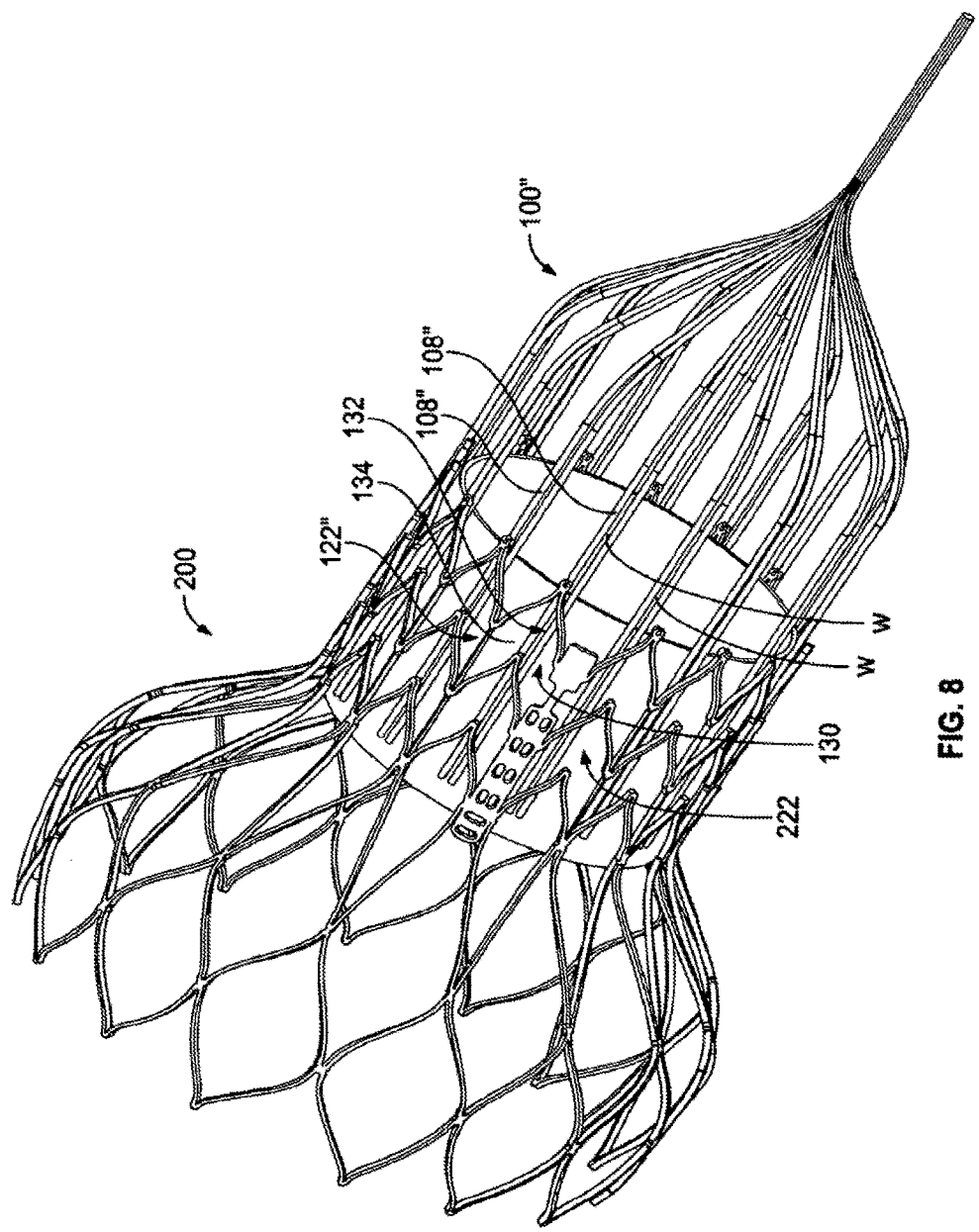
FIG. 8 is a perspective view of a crimping tool in accordance with still another embodiment of the present invention.

FIG. 8 shows another embodiment of a crimping tool 100" having tines 108" partially inserted within a prosthetic heart valve 200. The tines 108" divide the area of the cell openings 222 of prosthetic heart valve 200 into three or more portions. Crimping tool 100" may include 16 pairs of tines (as opposed to only 16 tines), wherein the tines 108" within a pair are spaced relatively close to one another. The tines 108" in a pair may extend over a single cell opening 222 and divide the area of the cell opening into three sections: a first peripheral section 130, a second middle section 132 between a closely-spaced pair of tines 108", and a third peripheral section 134. It is to be appreciated that the width W of each middle section 132 is defined by the distance between the closely-spaced tines in a pair, which can vary significantly. Width W may be selected so that a single cell opening 222 is divided into sections of different width or into three sections which are substantially the same width. In either case, the distance between the tines in a pair of tines may be less than the distance between adjacent pairs of tines, greater than the distance between an adjacent pair of tines, or the distances may be substantially the same.

Figure 9:
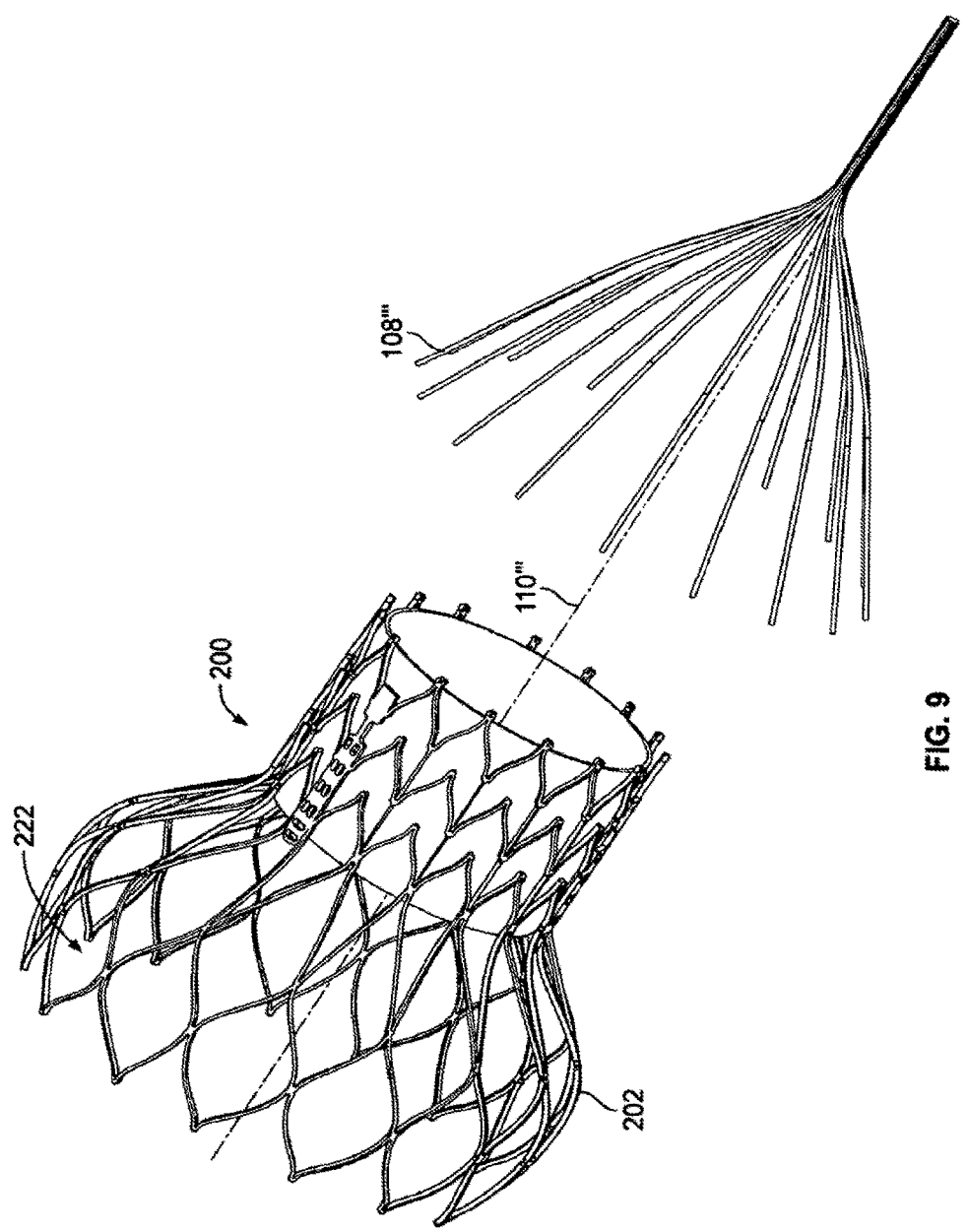
FIG. 9 is a perspective view of a crimping tool in accordance with yet another embodiment of the present invention.

Referring to FIG. 9, in yet another embodiment, a crimping tool 100''' may have tines 108''' that flare outwardly in an expanded state so that the crimping tool may be positioned around the exterior of the prosthetic heart valve 200. In such embodiment, the tines 108''' may be assembled to overlie the cell openings 222 of the stent 202. When the crimping tool 100''' is positioned around the prosthetic heart valve 200, the crimping tool 100''' and prosthetic heart valve 200 may be collapsed using the methods described above. When the tines 108''' are collapsed, they may move from an outwardly flared condition to a condition in which they are substantially parallel with one another and with the longitudinal axis 110''' of the crimping tool.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method for collapsing a prosthetic heart valve having a stent frame with a plurality of cell openings, and a valve structure disposed within the stent frame, the method comprising:

providing a crimping tool having a plurality of tines including a plurality of tine pairs defining an array around a longitudinal axis, each of the tines being a member of one the tine pairs, a distance between the tines in each of the tine pairs being less than a distance between adjacent tine pairs, the array having a first cross-sectional size in an expanded state and a second cross-sectional size less than the first cross-sectional size in a collapsed state;

assembling the crimping tool to the prosthetic heart valve so that the plurality of tines intersect the cell openings to divide the cell openings into first and second sections; and applying a radially inward force to the prosthetic heart valve to collapse the prosthetic heart valve while the crimping tool is assembled thereto.

2. The method as claimed in claim 1, wherein the step of applying a radially inward force moves the plurality of tines from the expanded state to the collapsed state.

3. The method as claimed in claim 1, wherein the step of applying a radially inward force to the prosthetic heart valve includes advancing a ring along the array so as to move the plurality of tines from the expanded state to the collapsed state.

4. The method as claimed in claim 1, wherein at least some of the plurality of cell openings have apexes, the assembling step including assembling the crimping tool to the prosthetic heart valve so that at least some of the plurality of tines intersect the apexes.

5. The method as claimed in claim 1, wherein the assembling step further includes inserting the plurality of tines between the valve structure and the stent frame.

6. The method as claimed in claim 1, wherein the assembling step further includes positioning the plurality of tines around an exterior of the stent frame.

7. The method as claimed in claim 1, further comprising removing the crimping tool from the prosthetic heart valve.

\* \* \* \* \*